(12) United States Patent
Averbuch

(10) Patent No.: US 10,406,325 B2
(45) Date of Patent: Sep. 10, 2019

(54) DIRECTIONAL ANCHORING MECHANISM, METHOD AND APPLICATIONS THEREOF

(75) Inventor: Dorian Averbuch, Ramat HaSharon (IL)

(73) Assignee: COVIDIEN LP, Mansfield, MA (US)

( * ) Notice: Subject to any disclaimer, the term of this patent is extended or adjusted under 35 U.S.C. 154(b) by 567 days.

(21) Appl. No.: 13/475,836

(22) Filed: May 18, 2012

(65) Prior Publication Data
US 2012/0232475 A1 Sep. 13, 2012

Related U.S. Application Data

(60) Division of application No. 12/271,175, filed on Nov. 14, 2008, now Pat. No. 8,764,725, which is a (Continued)

(51) Int. Cl.
*A61M 25/04* (2006.01)
*A61M 25/10* (2013.01)
(Continued)

(52) U.S. Cl.
CPC ............ *A61M 25/04* (2013.01); *A61M 25/10* (2013.01); *A61M 25/1011* (2013.01); *A61B 2017/22071* (2013.01); *A61M 25/0105* (2013.01); *A61M 25/0133* (2013.01); *A61M 37/0069* (2013.01); *A61M 2025/0057* (2013.01); *A61M 2025/0089* (2013.01); *A61M 2025/105* (2013.01); *A61M 2025/1013* (2013.01); *A61M 2025/1075* (2013.01); *A61M 2025/1081* (2013.01)

(58) Field of Classification Search
CPC .................. A61M 25/04; A61M 25/10; A61M 2025/1013; A61M 2025/105; A61M 2025/1075; A61M 2025/0096; A61M 25/0133; A61M 25/0152; A61M 25/0155; A61M 25/1002; A61M 2025/1047; A61M 2025/1059; A61M 2025/1093; A61M 29/00; A61M 37/0069; A61M 25/1011; A61M 2025/0293; A61B 2017/22071; A61B 2017/22077; A61B 2017/3484
USPC ........................................................ 604/96.01
See application file for complete search history.

(56) References Cited

U.S. PATENT DOCUMENTS 4,637,396 A * 1/1987 Cook ............................ 606/194
4,747,405 A * 5/1988 Leckrone ......................... 606/7
(Continued)

OTHER PUBLICATIONS

United States Patent and Trademark Office, Final Office Action dated May 26, 2011 in U.S. Appl. No. 12/271,175, 7 pages.
(Continued)

*Primary Examiner* — Bhisma Mehta
*Assistant Examiner* — Laura C Schell

(57) ABSTRACT

An anchoring mechanism and method for anchoring a device within a biological conduit include an expandable element configured for retaining the device at a desired angle relative to a central axis of the biological conduit. A steering mechanism is preferably provided for orienting the device prior to operation of the anchoring mechanism. The anchoring mechanism and method are employed in drug delivery devices, brachytherapy devices or for anchoring a catheter or sheath to provide a working channel for reliable guidance of a wide range of tools to a target location within the body.

13 Claims, 13 Drawing Sheets

Related U.S. Application Data continuation-in-part of application No. 10/597,747, filed as application No. PCT/IL2005/000159 on Feb. 9, 2005, now abandoned.

(60) Provisional application No. 60/542,280, filed on Feb. 9, 2004.

(51) Int. Cl.
  *A61M 25/01* (2006.01)
  *A61M 37/00* (2006.01)
  *A61M 25/00* (2006.01)
  *A61B 17/22* (2006.01)

(56) References Cited

U.S. PATENT DOCUMENTS

| | | | |
|---|---|---|---|
| 4,994,069 A | | 2/1991 | Ritchart et al. |
| 5,041,093 A | * | 8/1991 | Chu .................. 604/104 |
| 5,195,955 A | * | 3/1993 | Don Michael .......... 604/22 |
| 5,423,804 A | * | 6/1995 | Kulick .................. 606/14 |
| 5,480,422 A | | 1/1996 | Ben-Haim |
| 5,509,900 A | * | 4/1996 | Kirkman ............... 604/104 |
| 5,522,815 A | | 6/1996 | Durgin, Jr. et al. |
| 5,558,091 A | | 9/1996 | Acker et al. |
| 5,662,671 A | * | 9/1997 | Barbut et al. .......... 606/170 |
| 5,713,853 A | | 2/1998 | Clark et al. |
| 5,729,129 A | | 3/1998 | Acker |
| 5,752,513 A | | 5/1998 | Acker et al. |
| 5,766,151 A | * | 6/1998 | Valley ............. A61B 17/00234 604/103.07 |
| 5,814,064 A | * | 9/1998 | Daniel ............. A61B 17/22031 606/159 |
| 5,840,067 A | * | 11/1998 | Berguer ............. A61M 25/04 604/104 |
| 5,868,708 A | * | 2/1999 | Hart ................. A61M 25/1002 604/101.05 |
| 5,879,499 A | * | 3/1999 | Corvi ................ A61M 25/0012 156/173 |
| 5,928,248 A | | 7/1999 | Acker |
| 6,016,439 A | | 1/2000 | Acker |
| 6,147,480 A | | 11/2000 | Osadchy et al. |
| 6,161,032 A | | 12/2000 | Acker |
| 6,201,387 B1 | | 3/2001 | Govari |
| 6,203,493 B1 | | 3/2001 | Ben-Haim |
| 6,211,666 B1 | | 4/2001 | Acker |
| 6,233,476 B1 | | 5/2001 | Strommer et al. |
| 6,261,260 B1 | * | 7/2001 | Maki .................. A61L 29/04 428/35.5 |
| 6,314,310 B1 | | 11/2001 | Ben-Haim et al. |
| 6,332,089 B1 | | 12/2001 | Acker et al. |
| 6,335,617 B1 | | 1/2002 | Osadchy et al. |
| 6,350,252 B2 | * | 2/2002 | Ray .................. A61B 17/3417 604/105 |
| 6,366,799 B1 | | 4/2002 | Acker et al. |
| 6,371,970 B1 | * | 4/2002 | Khosravi ............. A61F 2/01 606/194 |
| 6,373,240 B1 | | 4/2002 | Govari |
| 6,427,314 B1 | | 8/2002 | Acker |
| 6,453,190 B1 | | 9/2002 | Acker et al. |
| 6,484,118 B1 | | 11/2002 | Govari |
| 6,580,938 B1 | | 6/2003 | Acker |
| 6,591,129 B1 | | 7/2003 | Ben-Haim et al. |
| 6,618,612 B1 | | 9/2003 | Acker et al. |
| 6,650,927 B1 | | 11/2003 | Keidar |
| 6,690,963 B2 | | 2/2004 | Ben-Haim et al. |
| 6,712,842 B1 | | 3/2004 | Gifford, III et al. |
| 6,788,967 B2 | | 9/2004 | Ben-Haim et al. |
| 6,995,729 B2 | | 2/2006 | Govari et al. |
| 7,101,380 B2 | | 9/2006 | Khachin et al. |
| 7,182,756 B2 | | 2/2007 | Saeed et al. |
| 7,197,354 B2 | | 3/2007 | Sobe |
| 7,236,567 B2 | | 6/2007 | Sandkamp et al. |
| 7,286,868 B2 | | 10/2007 | Govari |
| 7,301,332 B2 | | 11/2007 | Govari et al. |
| 7,321,228 B2 | | 1/2008 | Govari |
| 7,324,915 B2 | | 1/2008 | Altmann et al. |
| 7,343,195 B2 | | 3/2008 | Strommer et al. |
| 7,353,125 B2 | | 4/2008 | Nieminen et al. |
| 7,357,795 B2 | | 4/2008 | Kaji et al. |
| 7,366,562 B2 | | 4/2008 | Dukesherer et al. |
| 7,370,656 B2 | | 5/2008 | Gleich et al. |
| 7,373,271 B1 | | 5/2008 | Schneider |
| 7,386,339 B2 | | 6/2008 | Strommer et al. |
| 7,397,364 B2 | | 7/2008 | Govari |
| 7,682,335 B2 | * | 3/2010 | Pepper et al. .......... 604/103.13 |
| 2001/0031919 A1 | | 10/2001 | Strommer et al. |
| 2002/0173689 A1 | | 11/2002 | Kaplan |
| 2003/0163154 A1 | * | 8/2003 | Miyata ................ A61M 25/10 606/192 |
| 2004/0097804 A1 | | 5/2004 | Sobe |
| 2004/0138548 A1 | | 7/2004 | Strommer et al. |
| 2005/0033149 A1 | | 2/2005 | Strommer et al. |
| 2005/0107688 A1 | | 5/2005 | Strommer |
| 2005/0197566 A1 | | 9/2005 | Strommer et al. |
| 2006/0015126 A1 | | 1/2006 | Sher |
| 2006/0058647 A1 | | 3/2006 | Strommer et al. |
| 2006/0064006 A1 | | 3/2006 | Strommer et al. |
| 2007/0167738 A1 | | 7/2007 | Timinger et al. |
| 2007/0167743 A1 | | 7/2007 | Honda et al. |
| 2007/0167806 A1 | | 7/2007 | Wood et al. |
| 2007/0287901 A1 | | 12/2007 | Strommer et al. |
| 2008/0097187 A1 | | 4/2008 | Gielen et al. |
| 2008/0125760 A1 | | 5/2008 | Gilboa |
| 2008/0132909 A1 | | 6/2008 | Jascob et al. |
| 2008/0132911 A1 | | 6/2008 | Sobe |
| 2008/0139915 A1 | | 6/2008 | Dolan et al. |
| 2008/0144909 A1 | | 6/2008 | Wiemker et al. |
| 2008/0147000 A1 | | 6/2008 | Seibel et al. |
| 2008/0154172 A1 | | 6/2008 | Mauch |
| 2008/0157755 A1 | | 7/2008 | Kruger et al. |
| 2008/0161682 A1 | | 7/2008 | Kendrick et al. |
| 2008/0162074 A1 | | 7/2008 | Schneider |
| 2010/0280540 A1 | * | 11/2010 | Streeter ............... A61F 2/01 606/200 |

OTHER PUBLICATIONS

United States Patent and Trademark Office, Office Action dated Oct. 4, 2010 in U.S. Appl. No. 12/271,175, 11 pages.

Schmarak, Itzhak, Gera Strommer and Uzi Eichler, U.S. Appl. No. 10/986,567, filed Nov. 10, 2014, specification and drawings as filed, 81 pages.

* cited by examiner

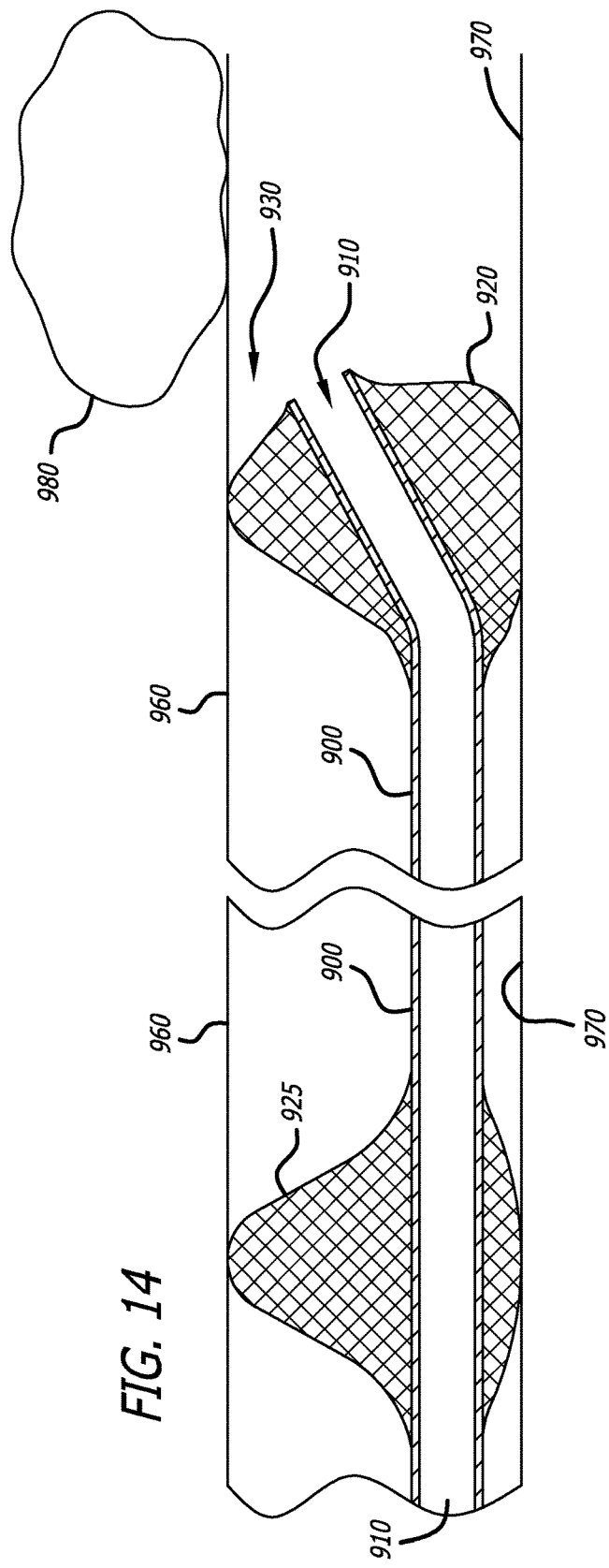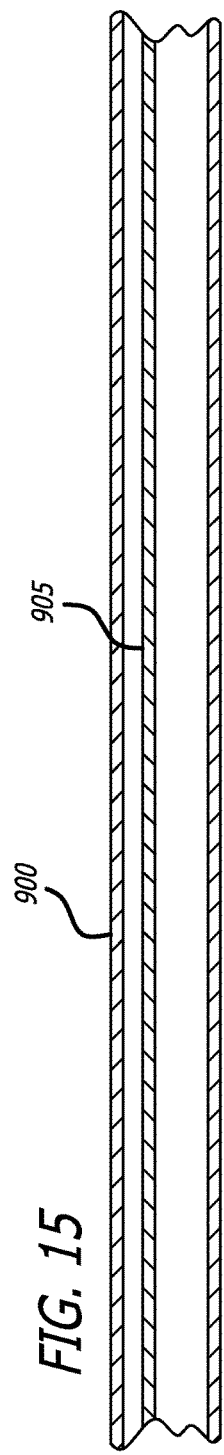
FIG. 14
FIG. 15

DIRECTIONAL ANCHORING MECHANISM, METHOD AND APPLICATIONS THEREOF

RELATED APPLICATIONS

This application is a divisional of U.S. patent application Ser. No. 12/271,175 filed Nov. 14, 2008 entitled Directional Anchoring Mechanism, Method And Applications Thereof, which is a continuation-in-part of U.S. application Ser. No. 10/597,747 filed Aug. 6, 2006 entitled Directional Anchoring Mechanism, Method And Applications Thereof, which is a National Phase of International Patent Application No. PCT/IL2005/000159, International Filing Date Feb. 9, 2005, entitled Directional Anchoring Mechanism, Method And Applications Thereof, which claims priority from U.S. Provisional Patent Application 60/542,280 filed Feb. 9, 2004 entitled Intrapulmonary Therapeutic Devices And A Directional Anchoring Mechanism, all of which are hereby incorporated herein by reference in their entireties.

BACKGROUND OF THE INVENTION

The present invention relates to intra-body anchoring mechanisms and, in particular, it concerns anchoring mechanisms and methods for anchoring a device at a desired angle relative to a biological conduit, and associated applications of such mechanisms in devices and methods.

One aspect of this invention deals with drug delivery. There are treatments for lung diseases for which the continuing application of drugs is required. One example is the treatment for destroying lung lesions. Although the drug is applied in a systemic manner to the entire body, it is concentrated inside cells having high metabolic activity. Beyond a certain level of concentration, the cell is destroyed. Cancerous cells, which are the target of such drugs, have such high metabolic activity. However there are additional body organs that attract the drug to concentrate in them. As a consequence, besides destroying the lesion, the drug also has a strong side effect of poisoning other organs in the body. There is an advantage to giving the medicine in high doses directly to the infected lung area either as a supplement or as a replacement to the traditional treatment.

Hence, there is an advantage of having a method and apparatus to apply a medicine or plurality of medicines directly to a certain location inside the lung, and furthermore to doing it continuously according to the required delivery profile.

FIG. 1 is a general description of the concentration of a drug in the patient's blood when the drug is given in doses. Every time the dose is given, the concentration is increased sharply and then decays over time. However the drug has the desired therapeutic effect only when its concentration in the blood is higher than a % and lower than b %, where a and b are individuals to the nature of the specific drug and patient condition. When the concentration is lower than a %, the drug is not sufficiently effective. When the concentration is higher than b %, the concentration is so high that it is likely to cause damage to the patient.

Therefore, it is preferred to give the drug constantly in order to keep its concentration within the patient's blood within the desired range. Devices for slow release or delayed release of drugs are well known in the art. An example is U.S. Pat. No. 3,760,984 to Theeuwes titled "Osmotically Powered Agent Dispensing Device With Filling Means", which is fully incorporated here by its reference. It describes a dual chamber capsule, with one chamber internal to the other. The internal chamber is formed of contractible foil and contains the drug to be delivered. The external chamber contains an osmotic solution. The outer layer is formed of a substance that is permeable to external fluid and impermeable to the internal solute. The osmotic pressure developed in the outer chamber contracts the internal layer and pushes the drug through an orifice.

The outer shape of the prior art devices is pre-shaped to the volume needed for containing the drug and the osmotic solution. Therefore they are not suitable for being delivered through the working channel of a bronchoscope which, for those in regular use by bronchoscopists, is less than 1.8 mm in diameter. Therefore it would be of benefit to have a drug delivery device that is sufficiently flexible and thin to be inserted through the working channel of the bronchoscope and can be directed through the pulmonary tree to a desired destination in the periphery of the lung, where the width of the bronchial airways is as small as 1 to 2 mm. It would also be of benefit to have a container for the drug which holds enough volume for long-term treatment and yet is able to pass through a sheath fine enough to enter airways of the aforementioned dimensions. It would also be of benefit to have an anchoring mechanism for securing the position of the device, once inserted, at its designated location for the duration of the treatment, while allowing its release and withdrawal after the treatment is done.

Brachytherapy or Seed implant is a technique of radiotherapy in which small seeds of radioactive materials implanted adjacent to the cancerous lesion. In the lung, this procedure is performed by inserting a thin flexible catheter via the working channel of the bronchoscope, into the designated lung airway, which is left there during the entire emission of the radiation. Since it is extremely inconvenient to remain for a long period of time with this catheter inserted through the bronchus, seeds emitting high dose radiation are often used to shorten the exposure time. This high-dose emission has the undesirable side effect of causing bleeding. On the other hand, using seeds of lower emission prolongs the treatment, which is undesirable too.

Often drugs are given to the patient as part of this treatment such as antibiotics and pain relief. Hence, in certain conditions it might be of benefit to incorporate brachytherapy in conjunction with said drug delivery device.

Another aspect of the invention is the need for a directional anchoring mechanism when performing a pulmonary needle biopsy and other similar procedures.

Currently, needle biopsy is performed through the working channel of the bronchoscope. First, the bronchoscope is guided through the pulmonary tree to the location where the biopsy has to be taken. Then, a flexible catheter having a biopsy needle at its distal tip is inserted through the working channel and punctured through the wall of the pulmonary passageway to the center of the lesion. This procedure is often dangerous because vital organs such as big blood vessels can be damaged if the needle mistakenly hits them. Guiding the needle according to 3 dimensional (3D) imaging data such as Computer Tomography (CT) data may avoid such damage.

PCT application WO 03/086498 to Gilboa, titled "Endoscopic Structures and Techniques for Navigating to a Target in Branched Structure", fully incorporated here by reference, describes methods and apparatus for navigating and leading bronchoscopic tools to the periphery of the lung in context of CT data. A steerable locatable guide, having a location sensor and a deflection mechanism incorporated at its distal tip, is inserted encompassed in a sheath and is used to navigate and place the distal tip of that encompassing sheath at a designated target location inside the lung.

This sheath is subsequently used effectively as an extension to the working channel of the bronchoscope to the periphery of the lung, where the bronchoscope itself cannot reach because of its thickness. First, registration between the CT data and the body of the patient is performed. Then, the locatable guide can be navigated through the branches of the pulmonary tree using the measured location coordinates of the guide's tip overlaid on the CT images. After bringing the tip to the target, the guide is withdrawn and a bronchoscopic tool is inserting into the empty sheath and pushed through it up to the target.

This method and apparatus may be used for bringing a biopsy needle to the target. The sheath has to have a diameter that is sufficiently large to allow insertion of tools through it, and yet sufficiently small for itself being inserted through the working channel of the bronchoscope. Therefore there is insufficient room for incorporating a steering mechanism as part of the sheath itself, and navigation should rely on the steering mechanism of the guide. When the tip is at the target, the guide has to be deflected in order to direct the end portion of the sheath toward the lesion, which is usually located at the side of the passageway. As a consequence, when the guide is withdrawn, the tip of the sheath loses its support, and might not be pointing to the direction of the target anymore. Hence it would be of benefit to have an anchoring mechanism for holding the tip of the sheath correctly oriented (angled) in the direction of the target, even when the guide with its steerable mechanism is withdrawn.

SUMMARY OF THE INVENTION

The present invention is an anchoring mechanism and method for anchoring a device at a desired angle relative to a biological conduit, and associated applications of such mechanisms in devices and methods.

According to the teachings of the present invention there is provided, a method for deploying and retaining a distal portion of a catheter within a biological conduit with a central axis of the distal portion of the catheter at a desired non-zero angle relative to a central axis of the conduit, the method comprising the steps of: (a) introducing the catheter into the biological conduit; (b) employing a steering mechanism at least temporarily associated with the distal portion of the catheter so as to deflect the distal portion of the catheter so that the central axis of the distal portion lies substantially at the desired non-zero angle relative to the central axis of the biological conduit; and (c) actuating an anchoring mechanism at least temporarily associated with the distal portion of the catheter, the anchoring mechanism including at least one expandable element configured to grip internal surfaces of the biological conduit in such a manner as to retain the distal portion of the catheter at the desired angle within the biological conduit.

According to a further feature of the present invention, the anchoring mechanism initially assumes a collapsed state having a first maximum diameter no more than 20 percent greater than an outer diameter of the distal portion of the catheter, the anchoring mechanism being expandable to an anchoring state in which the anchoring mechanism provides a plurality of contact regions disposed substantially on an ellipsoid profile so as to anchor the distal portion of the catheter within the biological conduit with the device axis at any desired angle within a pre-defined range of angles relative to the central axis of the conduit.

According to a further feature of the present invention, the anchoring state of the anchoring mechanism exhibits a maximum radial dimension, and wherein a distance from a distal end of the distal portion of the catheter to the anchoring mechanism is no greater than the maximum radial dimension.

There is also provided according to the teachings of the present invention, an anchorable device for deployment within a biological conduit at any desired angle within a pre-defined range of angles relative to a central axis of the conduit, the device comprising: (a) a catheter arrangement including a catheter and a steering mechanism for deflecting a distal portion of the catheter, the distal portion of the catheter having an outer diameter and defining a device axis; and (b) an anchoring mechanism at least temporarily associated with the distal portion of the catheter, the anchoring mechanism including at least one expandable element which initially assumes a collapsed state having a first maximum diameter no more than 20 percent greater than the outer diameter of the distal portion and which is expandable to an anchoring state in which the anchoring mechanism provides a plurality of contact regions disposed substantially on an ellipsoid profile so as to anchor the distal portion of the catheter within the biological conduit with the device axis at any desired angle within a pre-defined range of angles relative to a central axis of the conduit, wherein the anchoring state of the anchoring mechanism exhibits a maximum radial dimension, and wherein a distance from a distal end of the distal portion of the catheter to the anchoring mechanism is no greater than the maximum radial dimension.

According to a further feature of the present invention, the maximum radial dimension of the anchoring state of the anchoring mechanism is greater than the first maximum diameter in the collapsed state of the anchoring mechanism.

According to a further feature of the present invention, the steering mechanism is implemented as part of a guide element removably deployed within the catheter.

According to a further feature of the present invention, the guide element further includes a position sensor element forming part of a position measuring system for monitoring the position and attitude of the distal portion of the catheter within the biological conduit.

According to a further feature of the present invention, the anchoring mechanism includes an inflatable element, the catheter including at least one lumen deployed for introduction of a filler material into the inflatable element.

According to a further feature of the present invention, the inflatable element includes a first compartment for receiving a fluid therapeutic substance, the first compartment being in fluid communication with a dispensing arrangement.

According to a further feature of the present invention, the inflatable element further includes a second compartment for receiving an osmotic solution, the second compartment having at least one water permeable region.

According to a further feature of the present invention, the dispensing arrangement includes a cannula deployable so as to project substantially parallel to the device axis beyond the distal portion of the catheter, the cannula having an inlet in fluid communication with the first compartment.

According to a further feature of the present invention, the inflatable element is formed with a plurality of axial channels for allowing fluid flow along the biological conduit when in the anchoring state.

According to a further feature of the present invention, the inflatable element is formed with a plurality of external channels such that the inflatable element includes a plurality of lobes, thereby allowing fluid flow along the biological conduit between the lobes when in the anchoring state.

According to a further feature of the present invention, the anchoring mechanism includes a mechanical anchoring mechanism for deploying the plurality of contact regions from the collapsed state to the substantially ellipsoid profile.

According to a further feature of the present invention, there is also provided a carrier arrangement associated with the anchoring mechanism and carrying at least one brachytherapy seed.

According to a further feature of the present invention, the anchoring mechanism is configured to define a predefined non-zero angle between the distal portion of the catheter and the central axis of the biological conduit.

There is also provided according to the teachings of the present invention, a drug delivery device for deployment within a biological conduit and for delivering a drug into tissue adjacent to the biological conduit, the device comprising: (a) a first compartment for receiving a fluid therapeutic substance; (b) a cannula deployable so as to project from the device, the cannula having an inlet in fluid communication with the first compartment; (c) a second compartment for receiving an osmotic solution, the second compartment having at least one water permeable region; and (d) wherein the first compartment and the second compartment share a common displaceable wall such that absorption of water by the osmotic solution causes displacement of the displaceable wall so as to expel the fluid therapeutic substance from the first compartment along the cannula into the tissue.

According to a further feature of the present invention, the first and second compartments make up at least part of an inflatable anchoring device configured for retaining the device against walls of the biological conduit with the cannula projecting in a direction non-parallel to a central axis of the biological conduit.

According to a further feature of the present invention, the inflatable anchoring device assumes an anchoring state in which a plurality of contact regions are disposed substantially on an ellipsoid profile so as to anchor the drug delivery device within the biological conduit with the cannula projecting at any desired angle within a pre-defined range of angles relative to the central axis of the biological conduit.

BRIEF DESCRIPTION OF THE DRAWINGS

The invention is herein described, by way of example only, with reference to the accompanying drawings, wherein:

FIG. 14 illustrates schematically a mechanical variant of the anchoring mechanism of the present invention; and FIG. 15 illustrates schematically a mechanical variant of the catheter body of the present invention.

DETAILED DESCRIPTION OF THE INVENTION

Figure 1:
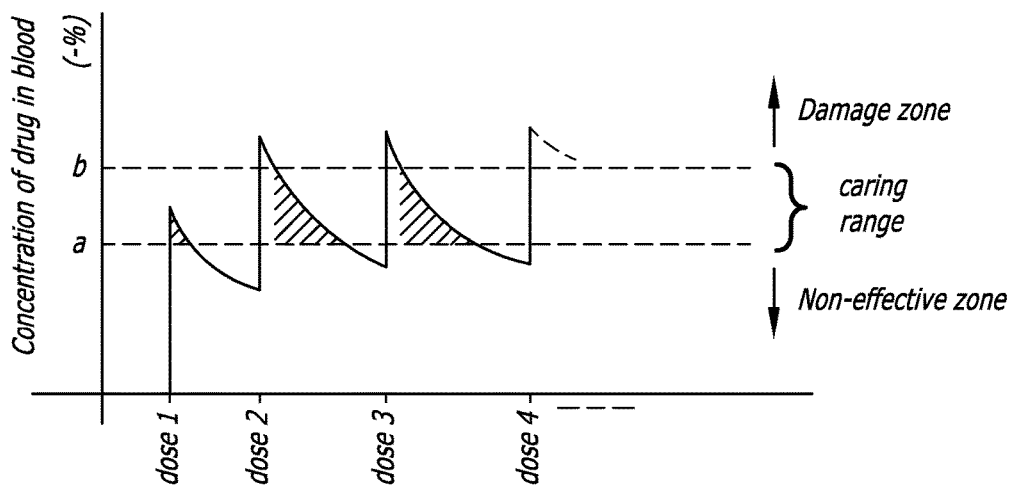
FIG. 1 is a graph illustrating time variations in the concentration of a drug in the blood where the drug is administered in sequential doses.

The present invention is an anchoring mechanism and method for anchoring a device at a desired angle relative to a biological conduit, and associated applications of such mechanisms in devices and methods.

The principles and operation of anchoring mechanisms and methods according to the present invention may be better understood with reference to the drawings and the accompanying description.

Referring now to the drawings, FIGS. 2-12 show various examples of anchorable devices, constructed and operative according to the teachings of the present invention, for deployment within a biological conduit at a desired angle relative to a central axis of the conduit. Generally speaking, in each case, the device includes a catheter arrangement including a catheter and a steering mechanism for deflecting a distal portion of the catheter. An anchoring mechanism, at least temporarily associated with the distal portion of the catheter, includes at least one expandable element which initially assumes a collapsed state for insertion and is expandable to an anchoring configuration for retaining the distal portion of the catheter at a desired angle.

The method of the present invention generally proceeds by introducing the catheter into the biological conduit and employing the steering mechanism to deflect the distal portion of the catheter so that the central axis of the distal portion lies substantially at the desired non-zero angle relative to the central axis of the biological conduit. The anchoring mechanism is then actuated so that at least one expandable element grips internal surfaces of the biological conduit in such a manner as to retain the distal portion of the catheter at the desired angle within the biological conduit.

In a preferred structural implementation, the collapsed state has a first maximum diameter no more than 20 percent greater than the outer diameter of the distal portion. The expandable element is expandable to an anchoring state in which the anchoring mechanism provides a plurality of contact regions disposed substantially on an ellipsoid profile so as to anchor the distal portion of the catheter within the biological conduit with the device axis at any desired angle within a pre-defined range of angles relative to a central axis of the conduit. In order to provide a relatively large range of anchoring angles, the distance from the distal end of the distal portion of the catheter to the distal end of the anchoring mechanism is preferably no greater than the maximum radial dimension of the anchoring mechanism when in its anchoring state.

At this stage, it will be appreciated that the anchoring mechanism of the present invention offers considerable advantages over conventional balloon or mechanical anchoring mechanisms. Specifically, the anchoring mechanism itself provides stabilization of the distal portion of the catheter not only axially but also in attitude (angularly) relative to the biological conduit, allowing the distal portion of the catheter (or a device associated therewith) to be directed reliably at a location in the wall of the conduit. This and other advantages of the apparatus and method of the present invention will become clearer from the detailed description below.

Before addressing the present invention in more detail, it will be useful to define certain terminology as used herein in the description and claims. Firstly, the invention is described for use in a "biological conduit". This phrase is used herein to refer to any tube-like structure within the human or animal body including, but not limited to, bronchial passageways, blood vessels and passageways of the digestive, renal and reproductive systems. Of particular importance are bronchial applications in which context the various applications of the present invention will be exemplified.

Reference is also made to "a plurality of contact regions" of the expandable element of the anchoring mechanism. It should be noted in this context that the "plurality of contact regions" may be discrete regions or may be regions of one or more continuous surface. In preferred cases, these regions are described as lying substantially on an "ellipsoid profile." The term "ellipsoid" is used herein loosely to refer to any configuration which appears primarily roughly oval as viewed in a side view. This terminology refers to a range of shapes including shapes approximating to spherical, an elliptical solid of revolution about the axis of the catheter with the major axis of the ellipse parallel to the catheter axis, an elliptical solid of revolution about the axis of the catheter with the minor axis of the ellipse parallel to the catheter axis, and various other structures in which outwardly-bowed elements are deployed around the distal portion of the catheter such as will be described below with reference to FIGS. 11A and 11B.

Reference is also made to a "maximum radial dimension" of the expandable element in its anchoring state. In the case of a roughly spherical expandable element, this is simply the radius of the sphere in its fully open state. In the case of a non-spherical ellipsoid, the maximum radial dimension is preferably defined to be half of the diameter of the fully open expandable portion measured perpendicular to the axis of the catheter. This distance is then used to define the proximity of the expandable portion to the distal end of the catheter, namely, that the part of the expandable element closest to the end of the catheter lies within a distance equal to the maximum radial dimension from the end of the catheter. Most preferably, the expandable portion terminates substantially at the end of the catheter, thereby maximizing the angular range of positions which can be accommodated. Preferably, the maximum radial dimension of the anchoring state of the anchoring mechanism is greater than the first maximum diameter in the collapsed state of the anchoring mechanism.

Finally with respect to definitions, reference is made to "osmotic solution" in the context of an osmotic pump drug delivery system of the present invention. The term "osmotic solution" is used herein to refer to any composition which creates an osmotic gradient relative to surrounding moisture or body fluids, thereby causing absorption of water and consequent volume increase in the osmotic solution. The principles of such pumps, and examples of materials suitable for implementing them, are well known in the field, for example, in the aforementioned U.S. Pat. No. 3,760,984 to Theeuwes.

Turning now to the various implementations of the present invention, it should be noted that the aforementioned catheter arrangement may either be an integral part of a device to be anchored, or some or all of its components may serve as a withdrawable deployment system. In most preferred examples, at least the steering mechanism is implemented as part of a guide element removably deployable within the catheter so as to leave an inner lumen of the catheter available for guiding additional tools or other devices to a target location.

One particularly preferred example of this functionality employs a guide element further including a position sensor element forming part of a position measuring system for monitoring the position and attitude of the distal portion of the catheter within the biological conduit. The resultant system is essentially as described in the aforementioned PCT application WO 03/086498 to Gilboa, titled "Endoscopic Structures and Techniques for Navigating to a Target in Branched Structure" with addition of the directional anchoring features of the present invention. This provides a greatly enhanced level of confidence that the guide has not shifted angularly during withdrawal of the guide element and insertion of a tool, thereby greatly improving the reliability of biopsy results or other procedures performed by the system.

Turning now to other examples of the present invention, FIGS. 2A-9 show various examples of a drug delivery system according to the teachings of the present invention. These examples illustrate implementation of the anchoring mechanism as one or more inflatable element, where the catheter arrangement defines at least one lumen deployed for introduction of a filler material into the inflatable element.

Figure 2A:
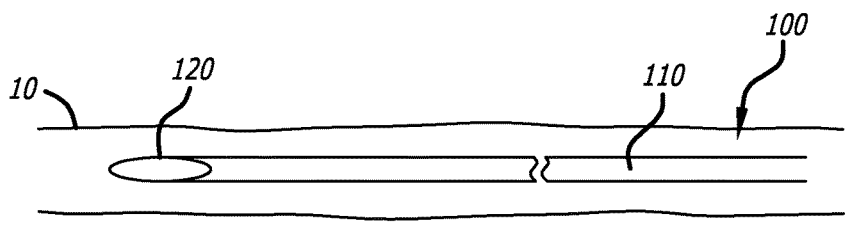
FIGS. 2A-2C illustrate schematically a slow drug delivery device, constructed and operative according to the teachings of the present invention, during deployment, filling and in operation, respectively.
Figure 2B:
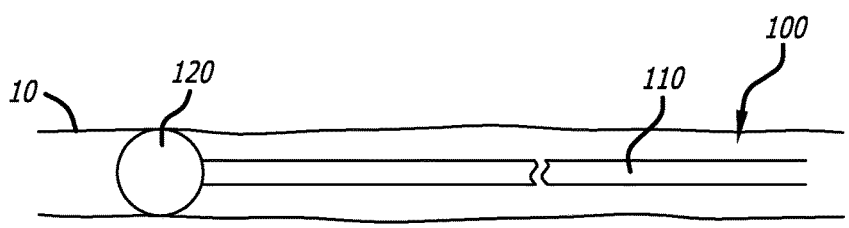
Figure 2C:
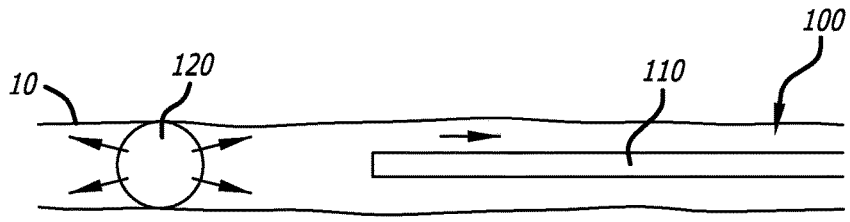

Specifically, FIG. 2a through 2c shows a general description of both method and apparatus of the drug delivery mechanism, according to this patent. A flexible thin catheter 100 has a body 110 and a drug delivery device 120 which is attached to the distal end of body 110. The device is inserted and navigated to a designated lung target in airway 10. While in insertion mode, as shown in FIG. 2a, the drug delivery device 120 is empty from drug and folded to have a diameter similar to the diameter of the catheter. After the device is located at the target, the drug, or drugs, are injected through the catheter and by filling device 120 inflating it as shown in FIG. 2b. The outer diameter of device 120 in the inflated mode is large enough to firmly press against the wall 10 of the airway. After complete inflation of the device, the catheter body 110 is parted from device 120 and withdrawn, as shown in FIG. 2c. The drug delivery device 120 is left in the airway, being held in place by the friction between the outer surface of the device and the airway wall. The drug is then released slowly from the device.

Figure 3:
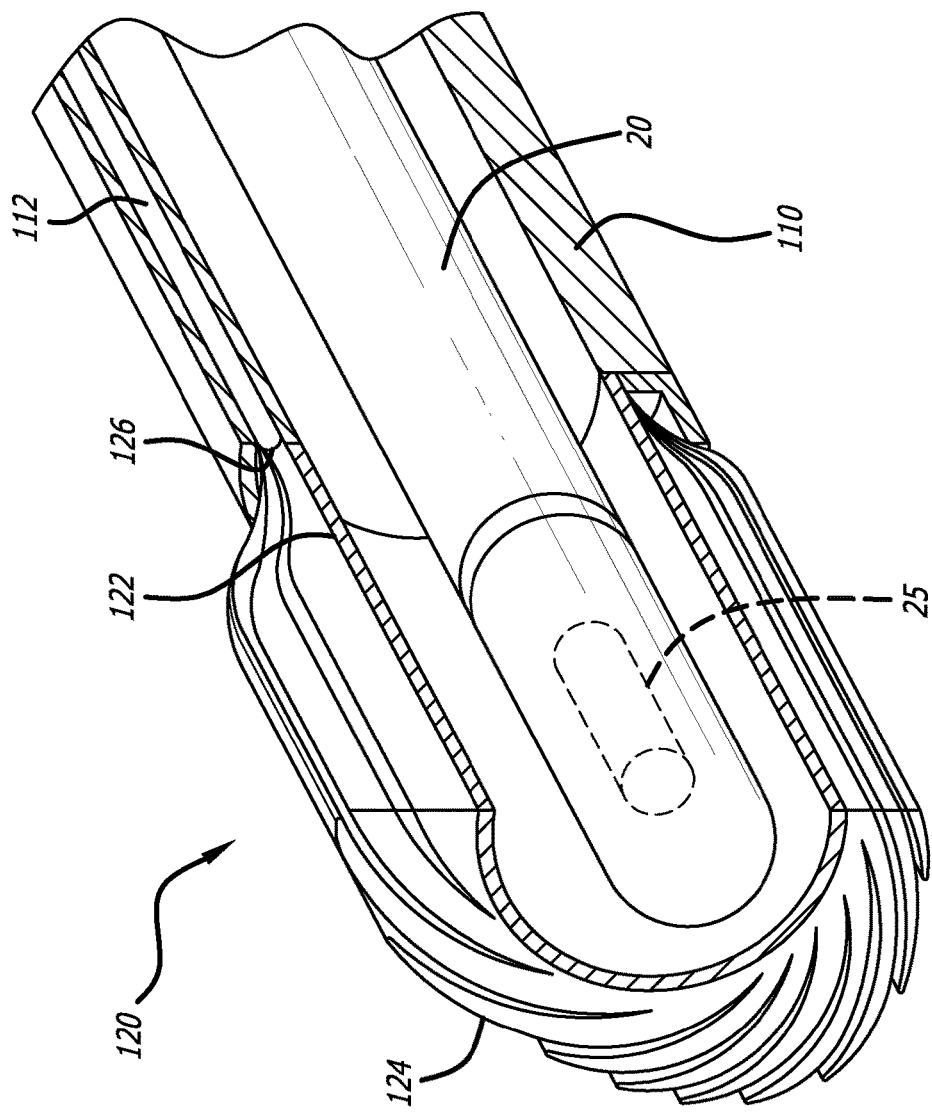
FIGS. 3 and 4 are schematic partially-cut-away isometric views of a first preferred implementation of the drug delivery device of FIGS. 2A-2C prior to and subsequent to deployment, respectively.
Figure 4:
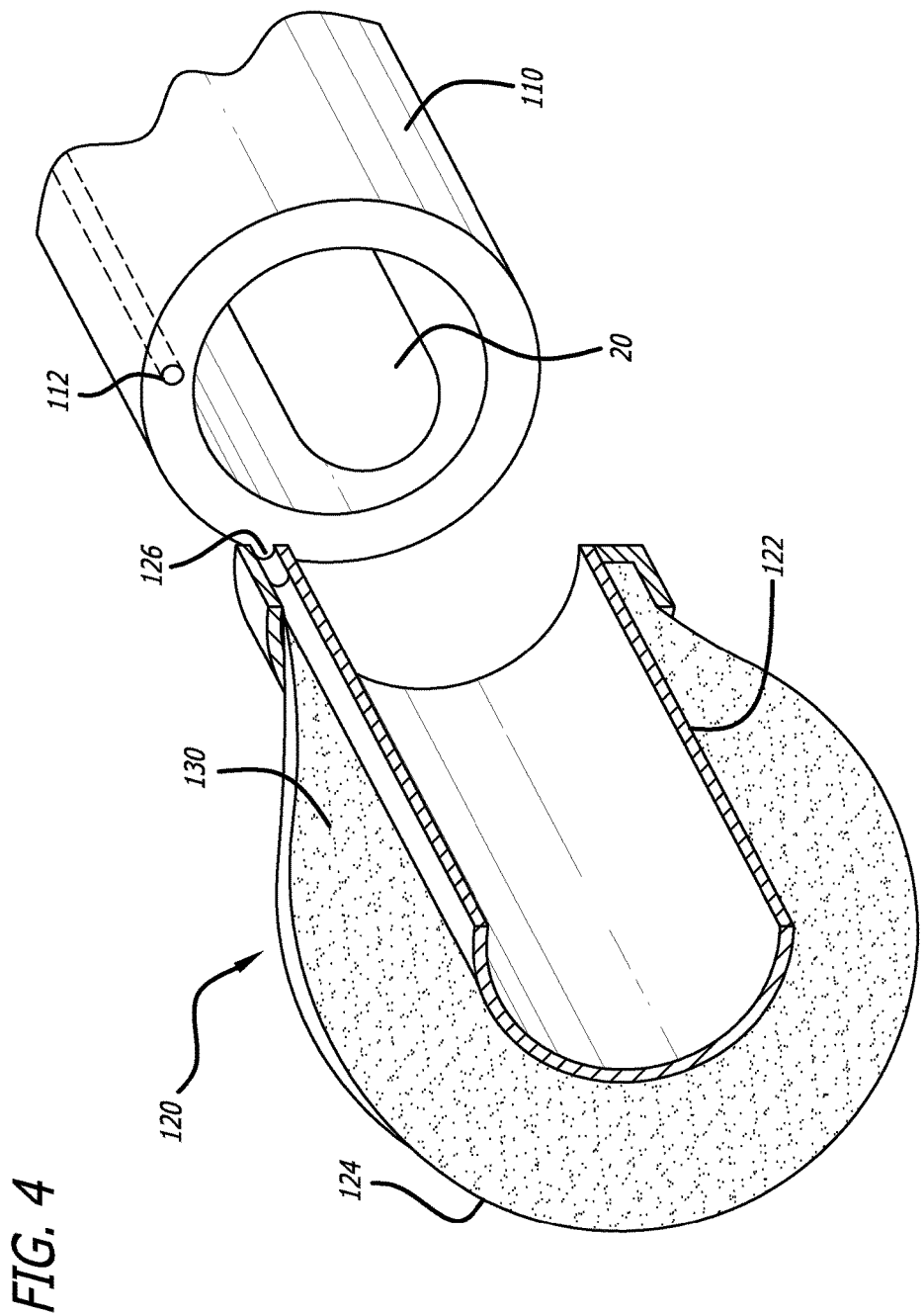

FIG. 3 shows a first embodiment of device 120. It is comprised of a cylindrical body 122, which is attached to catheter body 110. A balloon 124, made of relatively non-stretchable material such as Polyester or Nylon, is folded on tube 122 similar to the way an umbrella is folded. At least part of balloon 124 is made to be permeable to outer fluids. A steerable locatable guide 20, having a location sensor 25 at its distal tip as described in PCT application WO 03/086498, is inserted along the inner of body 112 and tube 122. A lumen 112 is implemented along body 110, which its orifice located inside balloon 124 through a valve 126. The drug, mixed with osmotic solution 130 is pressed through said lumen, to inflate balloon 124, as shown in FIG. 4. Body 110 together with the guide 20 can be detached from device 120.

Figure 5:
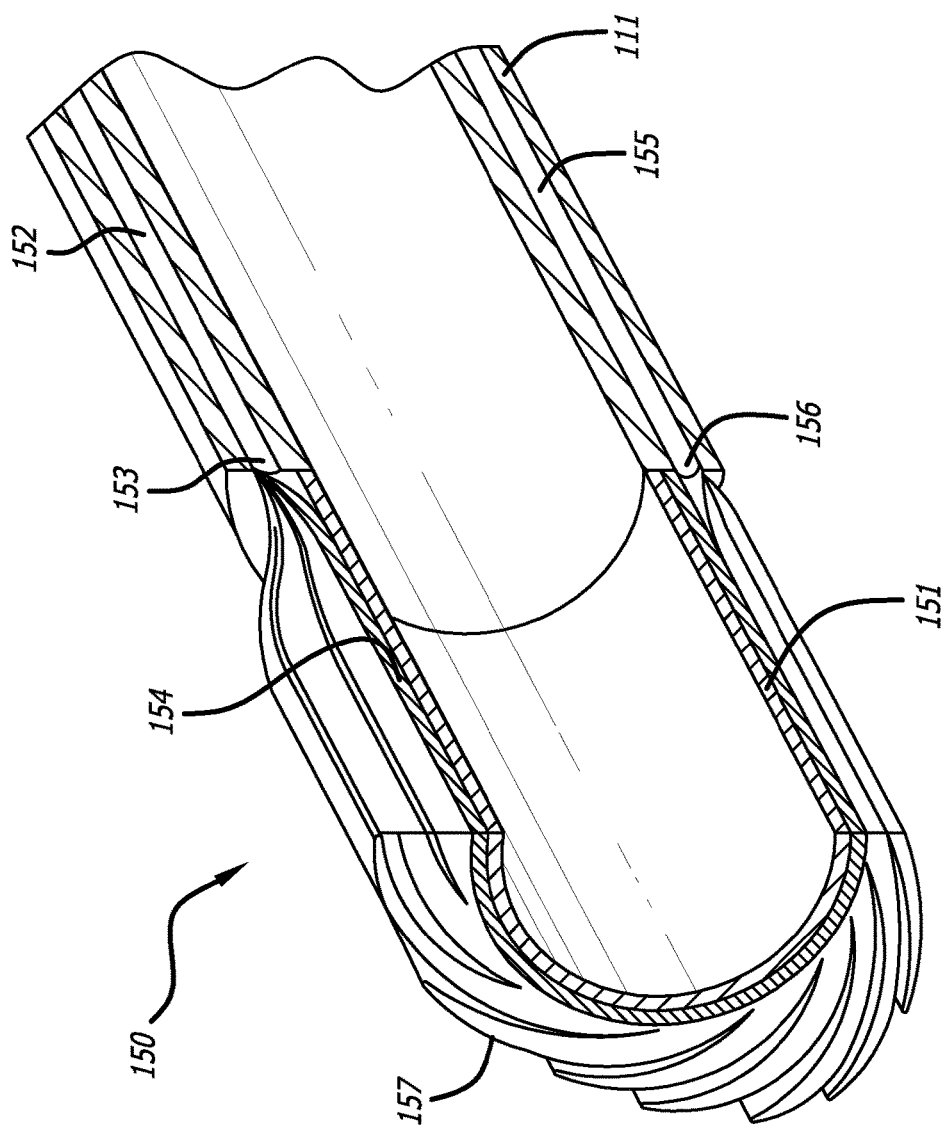
FIGS. 5 and 6 are schematic partially-cut-away isometric views of a second preferred implementation of the drug delivery device of FIGS. 2A-2C prior to and subsequent to deployment, respectively.

FIG. 5 shows an alternative device 150. A cylindrical body 151 attached to a hollow body 111. A first balloon foil 154 made of stretchable material such as Latex, enveloped cylinder 151. A drug solution 162 can fill the space between body 151 and foil 154 through a first lumen 152, which implemented along body catheter 111 and a valve 153. A second balloon foil 157, made of non-stretchable material, is enveloping the first balloon 154. Foil 157 made at least in part to be permeable to outer fluids.

Figure 6:
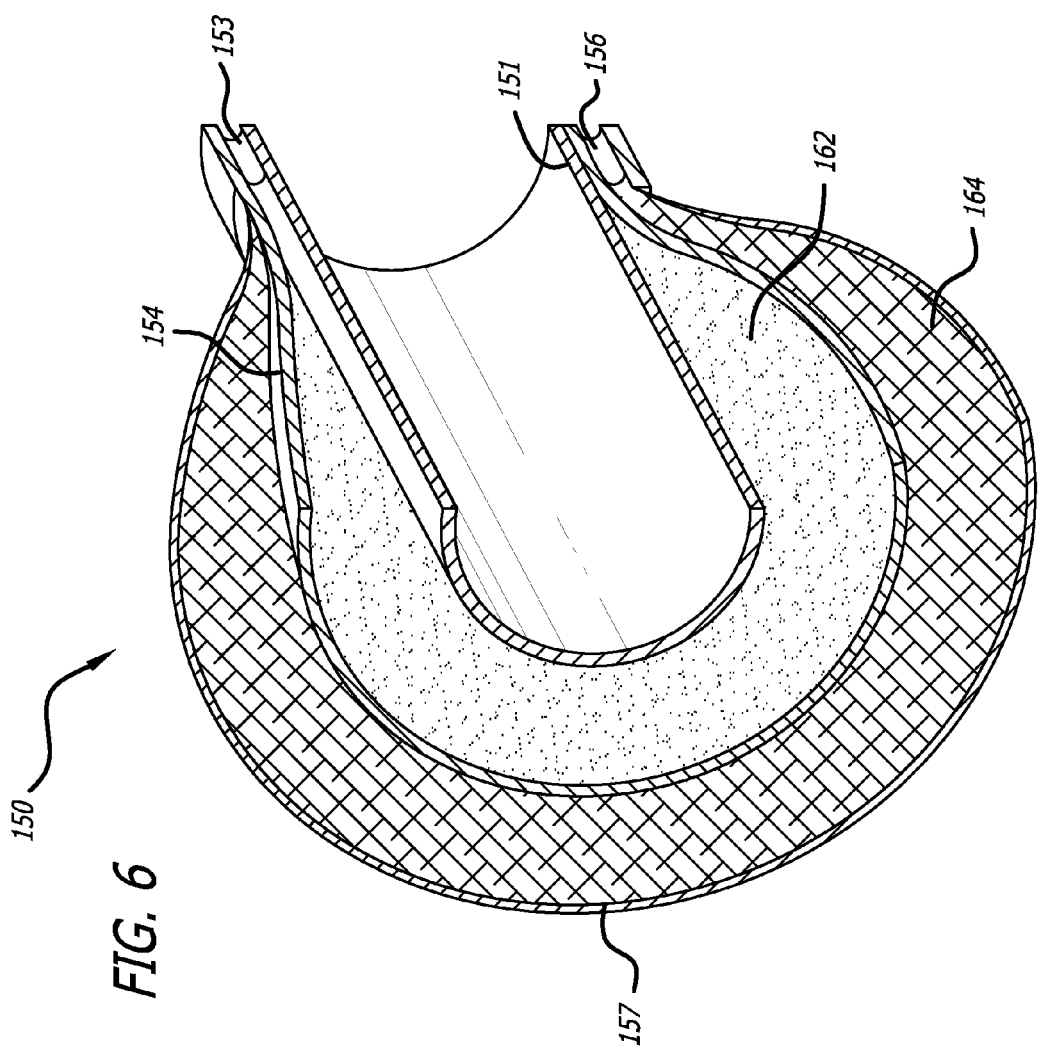

The latter may be filled with an osmotic solution 164 trough lumen 155, which is implemented along body catheter 111 and valve 156 as shown in FIG. 6.

After device 120 or the alternative device 150 are filled, inflated and detached from the body catheter, it works similarly to the device described in U.S. Pat. No. 3,760,984 and sold by ALZA, a company owned by Johnson & Johnson, under the name OROS-Oral Delivery Technology. The osmotic material either 130 or 164 cause fluids from outside of the device to flow inside and increase the internal osmotic pressure. This causes the drugs to drop out in a constant flow through an orifice (not shown). Because fluids from outside of the device replace the subtracted volume resulted from the dropped out drug, the balloon is not shrunk. Hence, while the balloon is kept intact, the device is kept secured in place.

It will be noted that the directional anchoring of the present invention may be of importance even in these needleless drug delivery devices, for example, where the drug release orifice is turned towards a specific target region so as to maximize the concentration of the drug adjacent to the target region.

In some procedures, it is required to inject the drug directly into the body tissue rather than release it at the lung airways. FIGS. 7a through 7d show an adaptation of the above-described method for using with an injection needle. As in FIGS. 5 and 6, the inflatable element here includes a first compartment for receiving a fluid therapeutic substance, and a second compartment having at least one water permeable region for receiving an osmotic solution. In this case, the device further includes a cannula deployable so as to project substantially parallel to the device axis beyond the distal portion of the catheter, the cannula having an inlet in fluid communication with the first compartment. Absorption of water by the osmotic solution causes displacement of a displaceable wall between the first and second compartments so as to expel the fluid therapeutic substance from the first compartment along the cannula into the tissue.

Figure 7A:
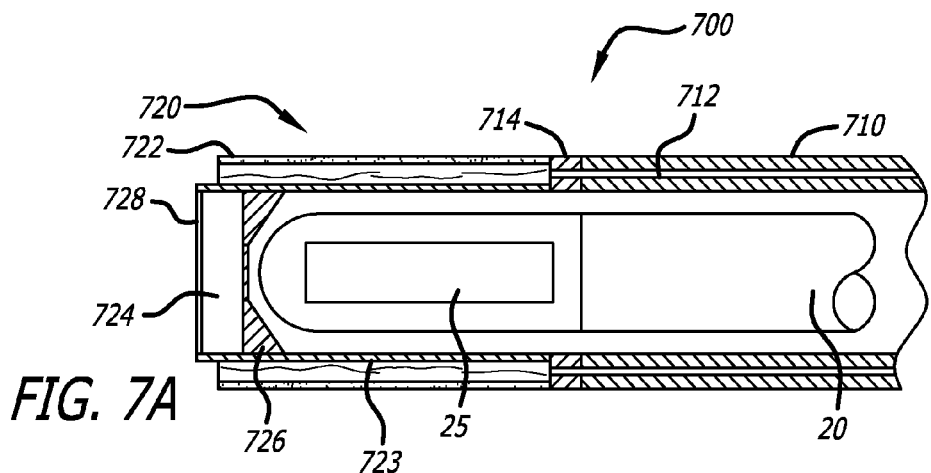
FIGS. 7A-7D are schematic cross-sectional views showing a third implementation of the drug delivery device of FIGS. 2A-2C employing a drug delivery cannula shown at four different stages of deployment.
Figure 7B:
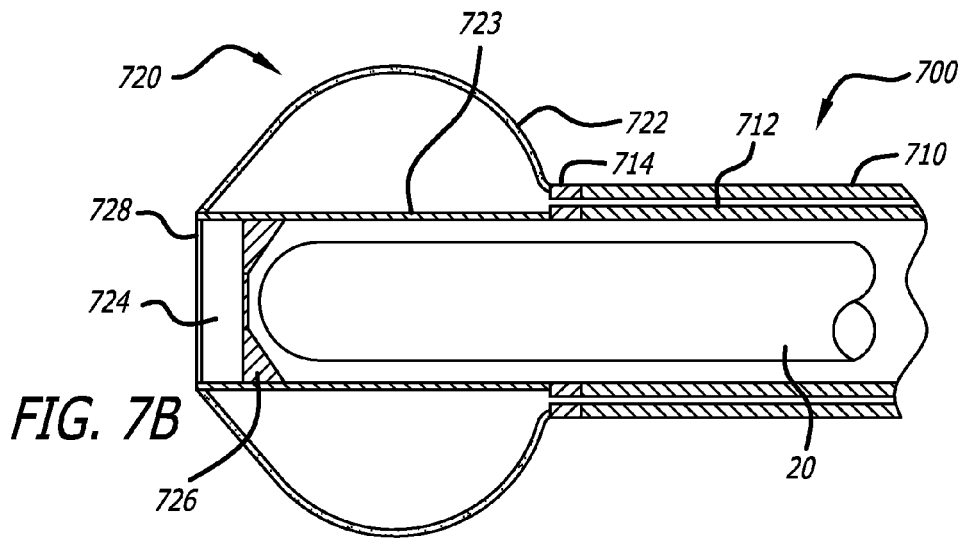
Figure 7C:
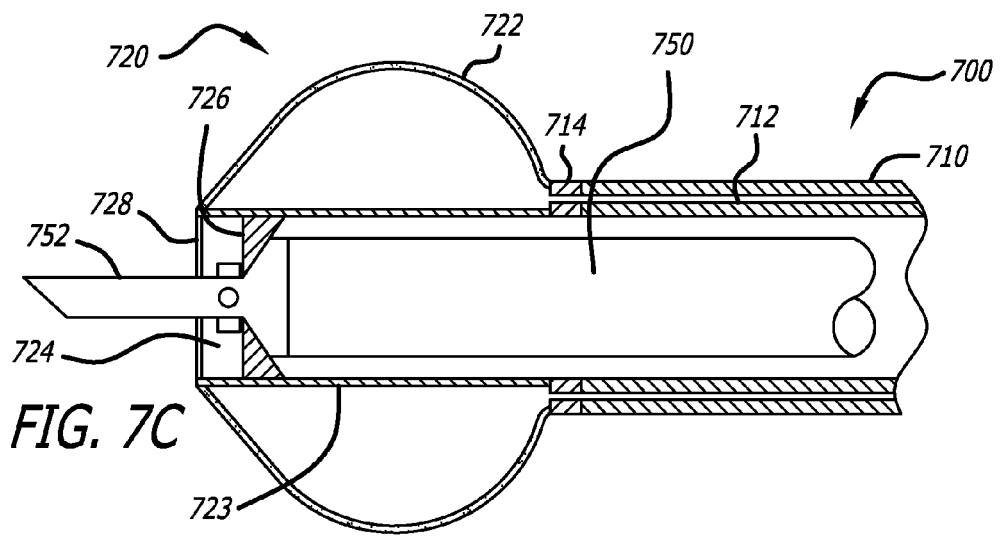
Figure 7D:
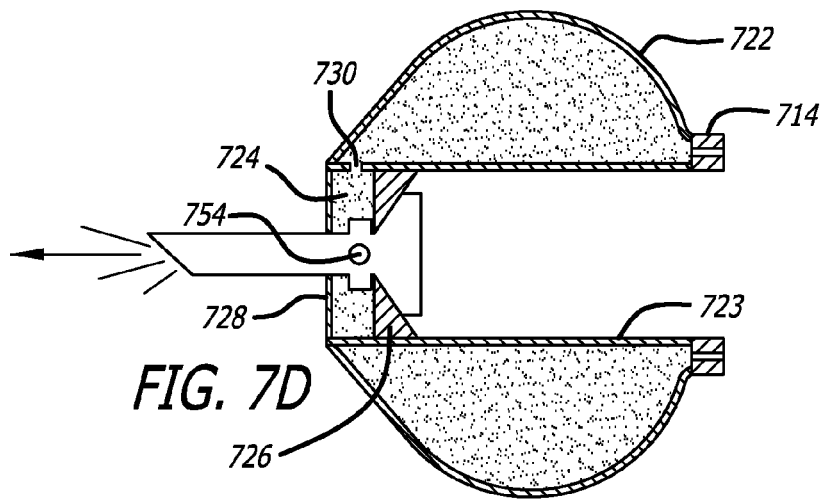

Reference is now made to FIG. 7a. A catheter 700 assembled of a catheter body 710 having one or more lumens 712, each terminating in a valve 714. A drug delivery device 720 attached to the distal tip of the catheter assembled from a cylindrical body 723, one or more balloons 722, identical to the above description balloons 124 or 154 and 157. At its distal end, it comprises an intermediate chamber 724, constructed of an internal valve 726 and a frontal foil 728. As before, a steerable locatable guide 20 having a location sensor 25 is used to navigate and placed the device 720 at its destination site. Using the plurality of lumen 712, the plurality of balloon 722 is filled and inflated, as shown in FIG. 7b. After the balloon is inflated, guide 20 is withdrawn and a needle (cannula) 752, which is mounted at the tip of guide 750, is inserted through the internal valve 726 which also locks the needle in place and through a puncture in the frontal foil 728, as shown in FIG. 7c, into the body tissue. FIG. 7d shows the said needle delivery device after guide 750 is dismantled and withdrawn. After osmotic pressure builds up inside the device the drug is slowly injected through orifice 730 between the frontal chamber 724 and the balloon, and through a hole 754 into the internal lumen of the needle.

Prior to the use of the needle, the device has to be directed towards the target.

Figure 8A:
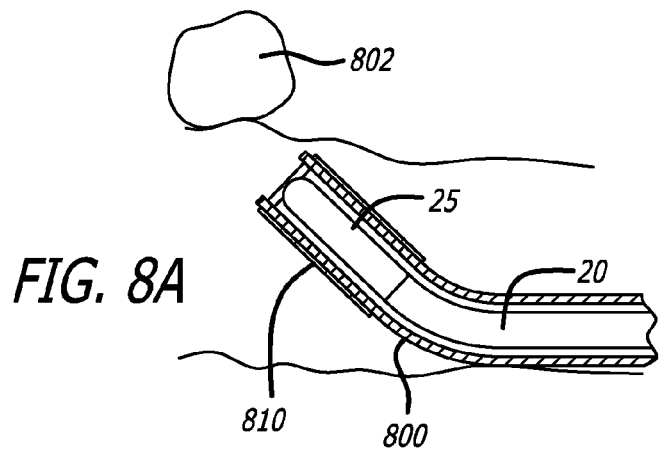
FIGS. 8A-8D illustrate schematically four stages of the deployment sequence of the device of FIGS. 7A-7D using a steerable catheter to provide a desired orientation of the cannula relative to the axis of a biological conduit.
Figure 8B:
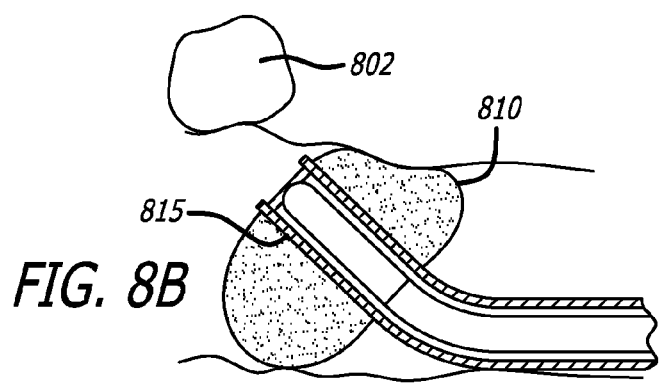
Figure 8C:
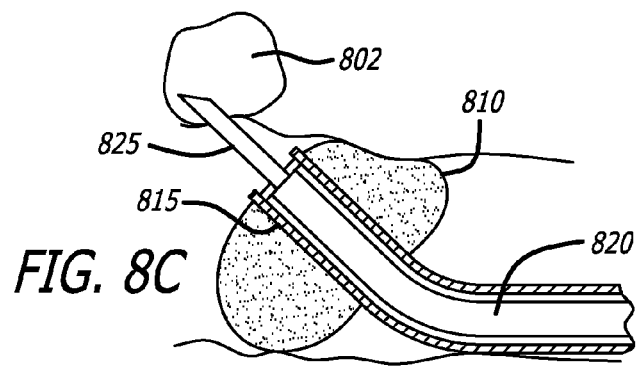
Figure 8D:
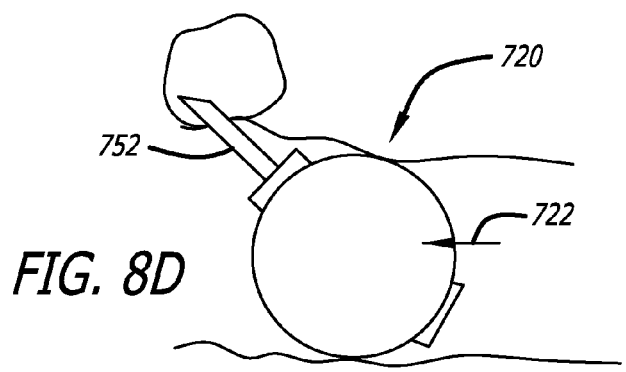

FIGS. 8a trough 8d describe a method of using a steerable-locatable guide in combination with a balloon to direct the insertion of a needle toward a designated target. A sheath 800, having an inflatable balloon 810 at its distal tip, is guided to a target 802 in the pulmonary tree using guide 20 and location sensor 25 as described in PCT application WO 03/086498. Upon reaching the target, guide 20 is deflected in the direction of target 802, as is seen in FIG. 8a. Holding the tip in that direction, balloon 810 is now inflated, as shown in FIG. 8b. The diameter of the balloon should be greater than the diameter of the airway by at least by 10%, preferably by 50%. The pressure exerted by the outer surface of the balloon 810 on the airway wall holds the internal tube 815 in the direction of target 802, allowing the guide 20 to be withdrawn and replaced by guide 825, as shown in FIG. 8c, and while tube 815 is maintaining its direction. In a first preferred embodiment, guide 825 incorporates a needle biopsy 825 at its distal tip. After taking the biopsy, the balloon is deflated and the sheath 800 is taken out together with the guide 820 and its needle 825. On a second preferred embodiment, the said sheath is the above described needle drug delivery device 700, the said balloon is the drug container 722 and the said needle is the injection needle 752. FIG. 8d shows the drug delivery device 720 after it is set to operate while its needle is directed into the target according to the method described herein.

As mentioned earlier, the above described method for directing and holding the distal end portion of a sheath can be used to direct various catheter tools towards a designated target in the body of the patient. Examples are biopsy tools such as forceps and biopsy needles, drug delivery tools such as sprayers and injection needles, RF and cryo ablating electrodes, light emitting probes for ablation or for photodynamic therapy, etc. Thus, in a generalized statement, the corresponding method of the present invention includes the steps of: inserting a steerable guide into the catheter lumen for navigating the catheter (sheath) to a target body portion, deflecting the steerable section of the guide so as to direct the end portion of the sheath towards said target body portion, and inflating the inflatable portion of the sheath in order to secure the direction of the sheath's distal end portion towards the target, even once the steerable guide is removed to free the lumen for insertion other catheter tools.

Figure 9:
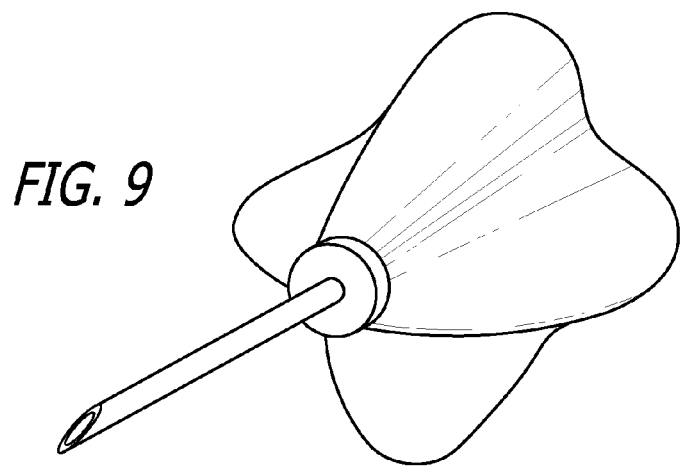
FIG. 9 is a schematic isometric view of a variant of the device of FIGS. 7A-7D wherein an inflatable anchoring mechanism is formed with a plurality of external channels.

The shape of the outer balloon according to this invention may be spherical or elliptical as mentioned. However in some cases it preferably has a modified shape in order to prevent blocking fluid flow along the biological conduit. In such cases, the inflatable element is preferably formed with a plurality of axial channels for allowing fluid flow along the biological conduit when in the anchoring state. In one preferred example, the inflatable element is formed with a plurality of external channels such that the inflatable element includes a plurality of lobes with the channels passing between them. FIG. 9 shows an example of such a balloon having channels along its length in order to allow air to flow around the balloon, while still having enough friction to secure the device in place. Alternative implementations may provide enclosed channels passing through the balloon (not shown).

Figure 10A:
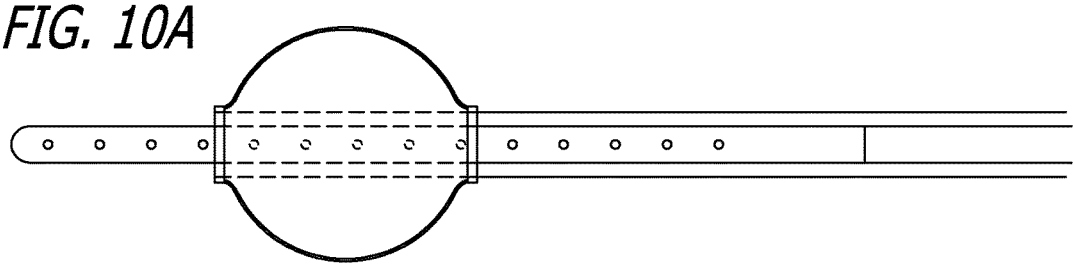
FIGS. 10A and 10B are schematic side views of a brachytherapy device employing an anchoring mechanism according to the teachings of the present invention during and subsequent to deployment, respectively.
Figure 10B:
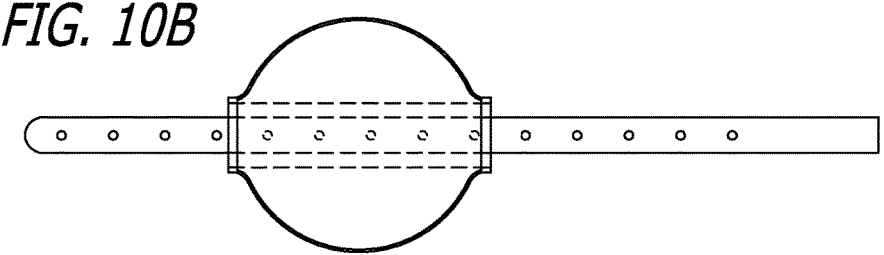

FIGS. 10A and 10B illustrate a further application of the present invention which includes a carrier arrangement associated with the anchoring mechanism and carrying at least one brachytherapy seed. Brachytherapy is a well-known method of killing a cancerous lesion by placing radioactive seeds adjacent to the lesion. The drug delivery device allows combining brachytherapy seed placement together with drug delivery while the drug can be selected to be one or more of the following: Chemotherapy, antibiotics, pain relief, gene therapy or other therapy. FIG. 10a shows how a thin catheter holding the seeds of the brachytherapy is placed into the drug delivery device, and in FIG. 10b how it is left secured by said device. Here too, the directional anchoring techniques provided by the present invention may be used to advantage for ensuring proximity between the brachytherapy seeds and the specific tissue to be targeted.

The above-described device may be built from biocompatible materials. It may be left in the body after its function is ended, or it may be released from its position and pulled out. The latter may be performed using the system and methods described in PCT application WO 03/086498 by navigating a bronchoscopic forceps to the device, puncturing the balloon and pulling it out exactly in the same technique currently used for removing foreign bodies from the lung.

Although illustrated thus far with reference to an inflatable element, it should be noted that most of the applications of the present invention may alternatively be implemented using a mechanical anchoring mechanism for deploying the plurality of contact regions from the collapsed state to the substantially ellipsoid profile. One non-limiting example of a mechanical anchoring mechanism is shown schematically in FIGS. 11A and 1 in.

Figure 11A:
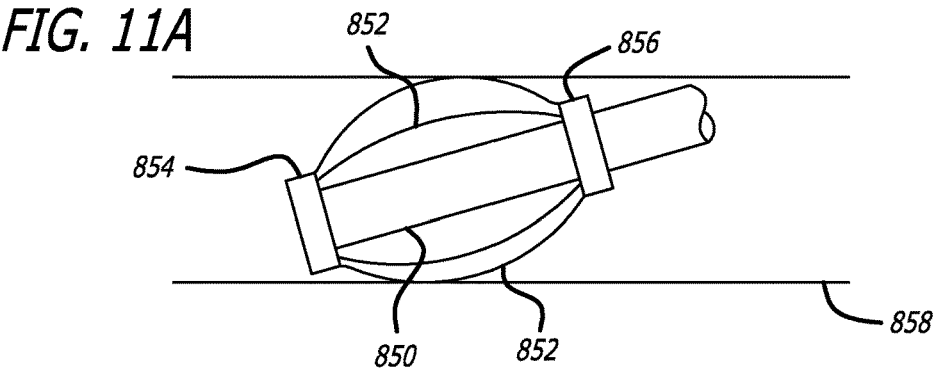
FIGS. 11A and 11B illustrate schematically a mechanical variant of the anchoring mechanism of the present invention.
Figure 11B:
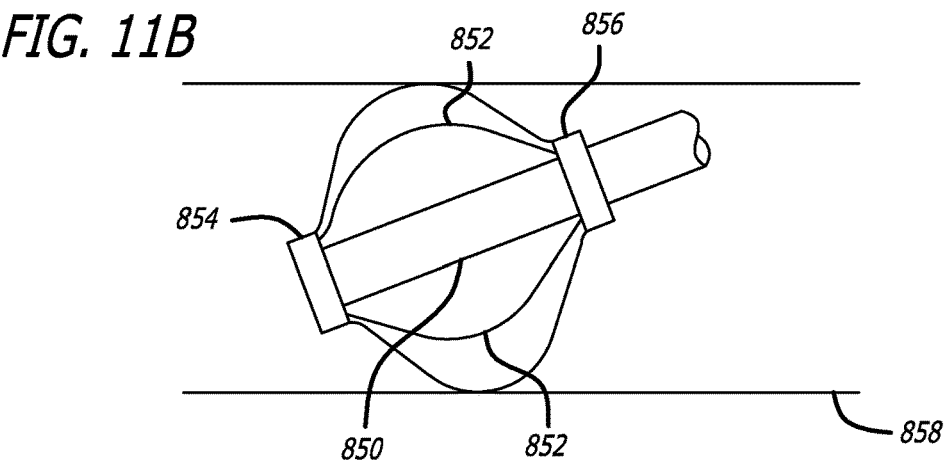

Specifically, the distal portion 850 of a catheter is here provided with a plurality of initially straight leaf spring elements 852 deployed between a pair of collars 854 and 856. An actuator (not shown) is configured to selectively displace one of the collars towards the other, thereby causing the leaf spring elements 852 to bow outwards so as to engage the wall of the biological conduit 858. The material of leaf spring elements 852 is chose, or the spring elements are coated, so as to produce high friction engagement with the conduit wall. FIGS. 11A and 11B show the use of this anchoring mechanism in conduits of different diameters, illustrating differing degrees of opening of the mechanism to accommodate the differing diameters. It will be appreciated that this mechanism also generates contact surfaces lying on a generally ellipsoid profile which are suited to retaining the catheter and/or an associated device at any desired angle within a range of angles relative to the axis of the biological conduit.

Figure 12:
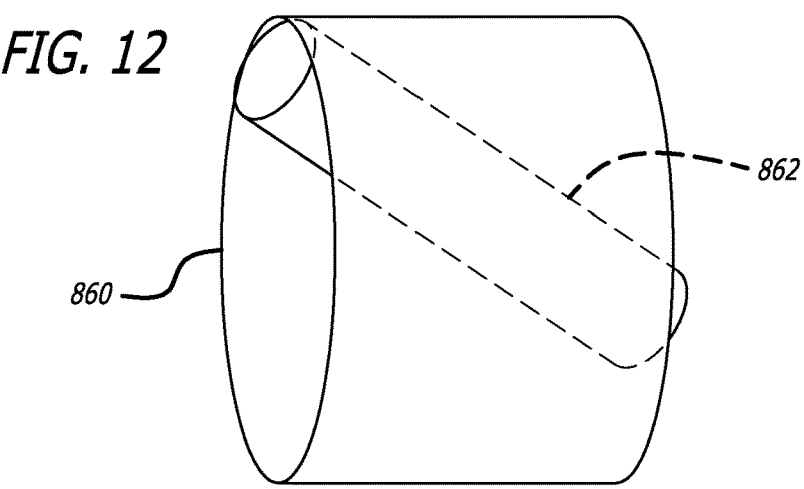
FIG. 12 illustrates schematically a fixed-angle anchoring mechanism for orienting and retaining a distal portion of a catheter at a predefined angle relative to the central axis of a biological conduit.

Turning finally to FIG. 12, it should be noted that the fine adjustment of angle of the distal portion of the catheter relative to the axis of the biological conduit is not required for all applications of the invention. Thus, in certain cases, it is sufficient to anchor the distal portion of the catheter at a predefined (non-zero) angle relative to the conduit axis, thereby ensuring an appropriate approach angle to a target region on or behind a side wall of the conduit. This can be achieved with a simple structure such as that illustrated schematically in FIG. 12.

Specifically, FIG. 12 shows a substantially cylindrical anchoring balloon 860 which tends to align itself when inflated with the direction of the biological conduit. The distal portion of a catheter 862 is mounted within anchoring balloon 860 with at least its tip at a predefined angle. Inflation of balloon 860 inherently orients the distal portion of the catheter facing towards the wall of the conduit at the predefined angle when the outer peripheral surface of the substantially cylindrical anchoring balloon 860 contacts an inner wall of the biological conduit. This may be performed even without provision of a steering mechanism, but is more preferably performed in a controlled manner by first employing a steering mechanism to direct the distal portion of the catheter at roughly the desired angle so that inflation of the balloon merely fixes the catheter in its position.

Balloon 860 may be implemented by generally known techniques. By way of non-limiting example, the balloon may be implemented as a folded balloon of flexible substantially inelastic (non-stretching) material. Alternatively, an elastic balloon which has variable wall thickness may be used to force the material to inflate selectively in the desired directions to achieve the non-coaxial inflated state.

Figure 13A:
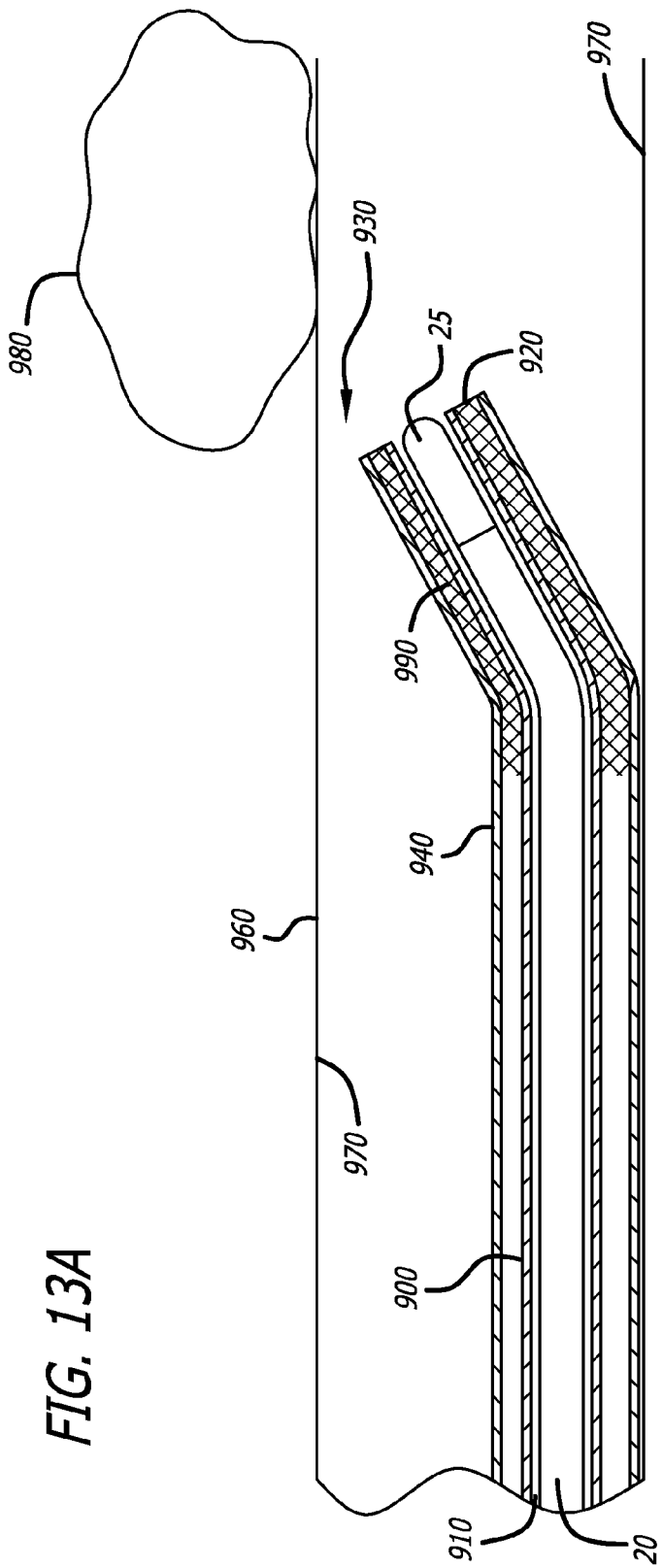
FIGS. 13A and 13B illustrates schematically a mechanical variant of the anchoring mechanism of the present invention.
Figure 13B:
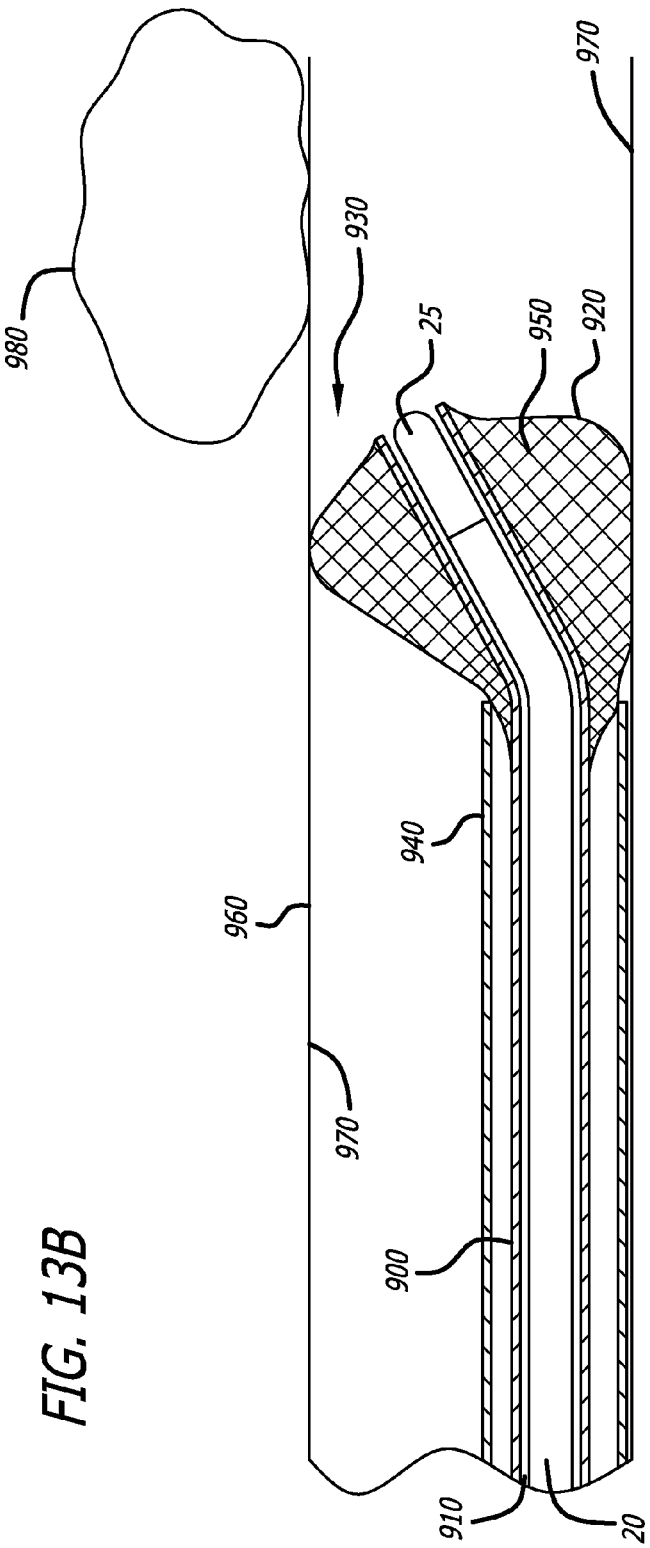

In yet another embodiment of the present invention, a variant of a mechanical anchoring mechanism may employ an expandable anchoring cage. With reference to FIGS. 13A and 13B, a steerable locatable guide 20, having a location sensor 25 at its distal tip, may be inserted along an inner lumen 910 of catheter body 900. The catheter body 900 may optionally employ a longitudinally oriented, visible or radio opaque marker 905 along its length or a portion thereof, as shown in FIG. 15.

An anchoring cage 920 is permanently associated or secured to the distal end 930 of catheter body 900. Anchoring cage 920 may encompass a bend in catheter body 900 positioned near distal end 930, as shown in FIG. 13A. In a collapsed or retracted state, illustrated in FIG. 13A, anchoring cage 920 may be retained by a retaining sheath 940 surrounding catheter body 900. To deploy the anchoring cage 920, the retaining sheath 940 is retracted from the distal end 930 of the catheter body 900. As the retaining sheath 940 is retracted, the filamentous members 950 (FIG. 13B) of anchoring cage 920 assume an expanded configuration. An example of an expanded or protracted anchoring cage 920 is illustrated in FIG. 13B, in which the bend in catheter body 900 is positioned in an interior of the expanded anchoring cage 920.

The anchoring cage 920 may, for example, comprise woven filamentous members 950. The filamentous members 950 may, for example, be constructed of a material such as stainless steel, Nitinol, or other suitable biocompatible material. The characteristics of retractability and expandability of the filamentous members 950 may be due to the elasticity or thermomechanical shape memory characteristics of the material from which the filamentous members 950 are made. It is noted that the plurality or singularity of the term "filamentous member(s) 950" is not intended to limit the configuration of the anchoring cage 950. For example, anchoring cage 920 may be constructed from a single contiguous filamentous element or from multiple independent or noncontiguous filamentous elements. The anchoring cage 920 may but need not be made of homogeneous filamentous elements 950, i.e. certain filamentous members 950 of the same anchoring cage 920 may be fabricated of different materials. The filamentous members 950 may have circular, elliptical, or asymmetrical cross-sectional shapes. The filamentous members 950 may further have longitudinal profiles that are either symmetrical, of equal or uniform width over the length of a single filament, or nonsymmetrical, of irregular width over the length of a single filament.

Upon expansion, the anchoring cage 920 acts against the interior wall 970 of the biological conduit 960. To further provide anchoring action, all or certain of the filamentous members 950 of the anchoring cage 920 may be textured, coated, or otherwise treated so as to produce a high friction engagement with the interior wall 970 of the biological conduit 960. The anchoring cage 920 may employ either a circular, elliptical, rectangular, triangular, or other symmetrical or nonsymmetrical expanded shape. As the retaining sheath 940 is retracted from the distal portion 930 of catheter body 900, expansion of the anchoring cage 920 may begin at the distal portion of anchoring cage 920, i.e. expansion may begin where the anchoring cage 920 is first exposed from retaining sheath 940. Alternatively, the anchoring cage 920 may be configured to selectively expand during or after retaining sheath 940 is fully retracted, e.g. expansion may begin at an approximate midpoint 990 of the anchoring cage 920 after the retaining sheath 940 has been fully transposed.

Similar to the embodiment illustrated in FIG. 12, in a mechanical anchoring mechanism of the present embodiment it may be sufficient to anchor the distal portion of the catheter body at a predefined angle relative to the biological conduit axis, thereby ensuring an appropriate approach angle to a target 980 on or behind the interior wall of the biological conduit (FIGS. 13A-14). In such a configuration, the anchor cage may be constructed in a shape similar to the shape illustrated in FIG. 12. Specifically, the mechanical anchoring mechanism may be a substantially cylindrical anchoring cage which, when expanded, tends to align itself with the direction of the biological conduit. Expansion of the anchoring cage would inherently orient the distal portion of the catheter body along the interior wall of the biological conduit at the predefined angle. This may be performed even without provision of a steering mechanism, but is more preferably performed in a controlled manner by first employing a steering mechanism to direct the distal portion of the catheter body at roughly the desired angle so that expansion of the anchoring cage merely fixes the catheter body in its position.

Certain embodiments of the present invention, as shown in FIG. 14, may employ one or more anchoring cages 925 positioned along the length of catheter body 900. The anchoring cages 925 are constructed and function in a manner substantially identical to those described above for the anchoring cage 920. The primary difference between anchoring cages 925 and 920 being that anchoring cage 920 is positioned at the distal end 930 of catheter body 900. In contrast, one or more of the anchoring cages 925 may be positioned along the length of catheter 900. The anchoring cages 925 function to secure the catheter 900 within the biological conduit 960 at multiple points and to thereby further decrease the possibility of the catheter 900 moving during a procedure.

It will be appreciated that an anchoring cage mechanism according to the present embodiment may provide certain advantages. First, once deployed, an anchoring cage may not substantially restrict the flow of fluids or air through the biological conduit in which the anchoring cage is utilized. This may allow for safer prolonged usage of the anchoring cage without the complications or risk associated with reduced flow in the biological conduit. Second, in contrast to an inflatable or balloon-type anchoring device, deployment or expansion of an anchoring cage does not require the translocation of an inflation substance, e.g. saline. This greatly simplifies the catheter design and reduces catheter manufacturing costs.

It will be appreciated that the above descriptions are intended only to serve as examples, and that many other embodiments are possible within the scope of the present invention as defined in the appended claims.

What is claimed is:

1. An instrument for deployment within a biological conduit comprising:
   a catheter defining a longitudinal axis, the catheter having a distal tip angled with respect to the longitudinal axis of the catheter to form a bend;
   a first expandable anchor comprising a first anchoring cage and extending from the distal tip to a location proximal of the bend, the first anchoring cage, the first anchoring cage annularly disposed about the catheter and configured to transition between an expanded state and a retracted state, wherein, in the expanded state, an outer peripheral surface of the first anchoring cage is configured to act against an internal surface of the biological conduit, and the distal tip of the catheter is oriented at a predefined non-zero angle relative to a central axis of the biological conduit, such that the distal tip is angled with respect to the longitudinal axis of the catheter towards a target region on or behind a wall of the biological conduit; and
   a second expandable anchor comprising a second anchoring cage and positioned proximal to the first expandable anchor, and the second anchoring cage configured to transition between an expanded state and a retracted state, at least one of the first or second anchoring cages configured to produce high friction engagement with the internal surface of the biological conduit while allowing fluid flow through the biological conduit when in the expanded state.

2. The instrument of claim 1, wherein at least one of the first or second anchoring cages comprises at least one filamentous element.

3. The instrument of claim 2, wherein the at least one filamentous element comprises a material selected from the group of materials comprising: stainless steel and Nitinol.

4. The instrument of claim 2, wherein the at least one filamentous element is woven.

5. The instrument of claim 1, wherein, in the expanded state, at least one of the first or second anchoring cages is configured to align itself in a predefined orientation relative to the central axis of the biological conduit.

6. The instrument of claim 1, wherein the catheter further comprises a sheath configured to retain at least one of the first or second anchoring cages in the retracted state.

7. The instrument of claim 1, further comprising a position sensor forming part of a position measuring system for monitoring a position and attitude of the distal tip of the catheter.

8. The instrument of claim 7, wherein the position sensor is associated with a steering mechanism operable to deflect the distal tip of the catheter.

9. The instrument of claim 8, wherein the steering mechanism is implemented as part of a guide element removably deployable within the catheter.

10. The instrument of claim 7, wherein the catheter further defines a lumen having the position sensor removably disposed therein.

11. The instrument of claim 1, wherein at least one of the first or second anchoring cages is biased towards the expanded state of the respective first or second anchoring cages.

12. The instrument of claim 1, wherein the first anchoring cage is configured to expand towards the expanded state of the first anchoring cage beginning from the distal tip of the catheter.

13. The instrument of claim 1, wherein at least one of the first or second anchoring cages is configured to expand towards the expanded state of the respective first or second anchoring cages beginning at a point proximal of the distal tip of the catheter.

\* \* \* \* \*